United States Patent
Feingold

(10) Patent No.: US 8,869,975 B2
(45) Date of Patent: Oct. 28, 2014

(54) LENS HOLDER APPARATUS AND SYSTEM AND METHOD

(75) Inventor: Vladimir Feingold, Laguna Niguel, CA (US)

(73) Assignee: Presbibio, LLC, Los Angeles, CA (US)

( * ) Notice: Subject to any disclaimer, the term of this patent is extended or adjusted under 35 U.S.C. 154(b) by 989 days.

(21) Appl. No.: 12/705,523

(22) Filed: Feb. 12, 2010

(65) Prior Publication Data

US 2011/0198242 A1   Aug. 18, 2011

(51) Int. Cl.
*A45C 11/04* (2006.01)
*A61J 1/00* (2006.01)
*A61F 2/16* (2006.01)
*A61F 2/00* (2006.01)

(52) U.S. Cl.
CPC ............... *A61J 1/00* (2013.01); *A61F 2/1662* (2013.01); *A61F 2/0095* (2013.01); *Y10S 134/901* (2013.01)
USPC ............. 206/5.1; 134/901; 206/205; 422/113

(58) Field of Classification Search
USPC .......... 206/5.1, 205, 438, 804, 493; 220/4.01, 220/4.21, 4.26; 623/6.11; 294/1.2; 606/107; 134/137, 901; 422/113, 300
See application file for complete search history.

(56) References Cited

U.S. PATENT DOCUMENTS

| | | | | |
|---|---|---|---|---|
| 4,423,809 A | * | 1/1984 | Mazzocco | 206/5.1 |
| 5,186,317 A | * | 2/1993 | Ryder et al. | 206/5.1 |
| 5,788,706 A | | 8/1998 | Deminski | |
| 5,972,292 A | * | 10/1999 | DeMeo | 422/25 |
| 6,536,586 B2 | | 3/2003 | Nakao et al. | |
| 2002/0029981 A1 | * | 3/2002 | Nigam | 206/5.1 |
| 2003/0038045 A1 | * | 2/2003 | Clausen | 206/308.1 |
| 2004/0173474 A1 | | 9/2004 | Haggin | |
| 2007/0000792 A1 | | 1/2007 | Newman et al. | |
| 2009/0026097 A1 | * | 1/2009 | Huang et al. | 206/308.2 |

* cited by examiner

*Primary Examiner* — Anthony Stashick
*Assistant Examiner* — Robert Poon
(74) *Attorney, Agent, or Firm* — Lawrence S. Cohen

(57) ABSTRACT

An apparatus for safely retaining an eye implant lens for transport and access for inspection and use in which a holding apparatus has a chamber for holding a lens. In one embodiment the chamber has aligned transparent portions and a lens can be placed in alignment with the transparent portions to enable inspection. Also, a system including the apparatus and a bottle assembly that will hold the apparatus in the bottle. A method for holding an eye implant lens in which a lens is placed in the apparatus which can then be placed in a bottle assembly.

8 Claims, 10 Drawing Sheets

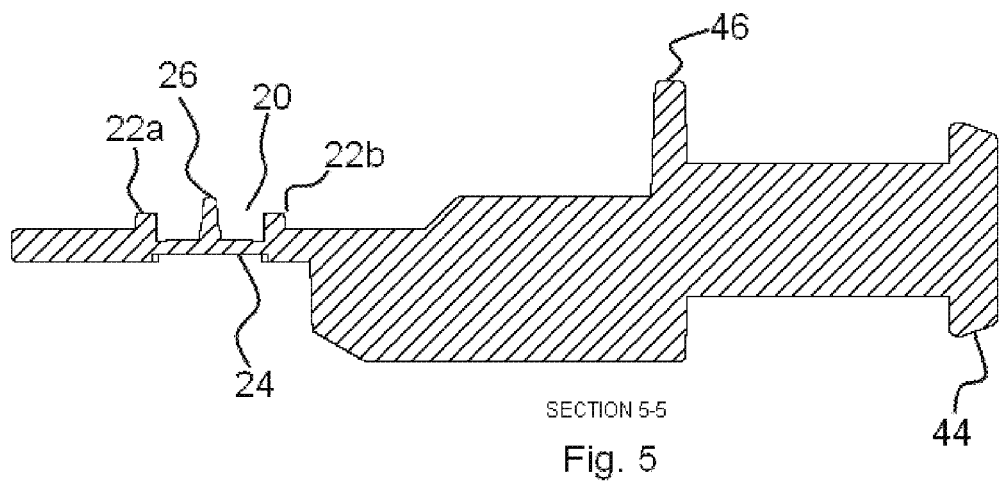
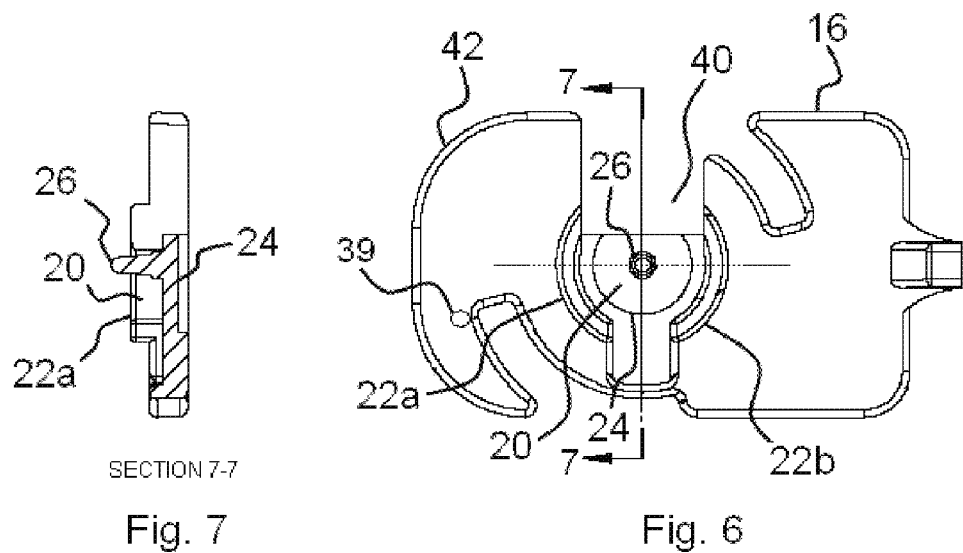

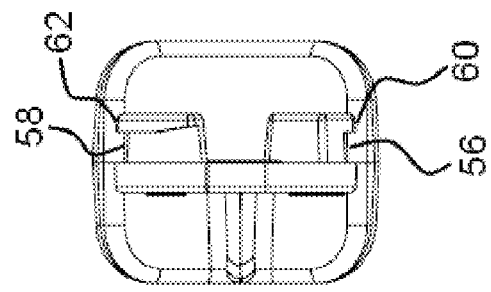
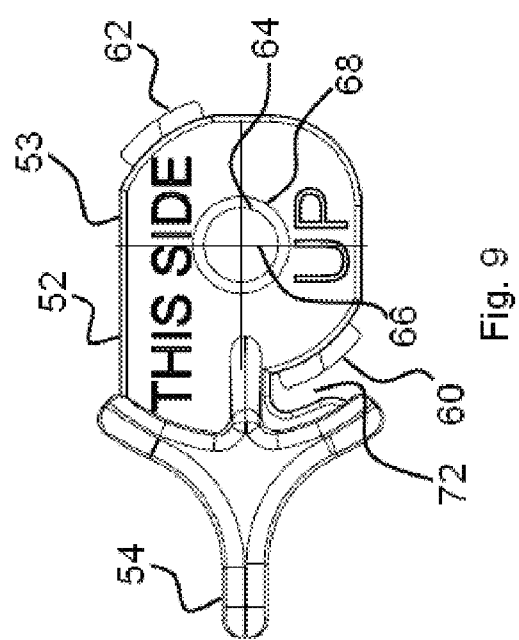
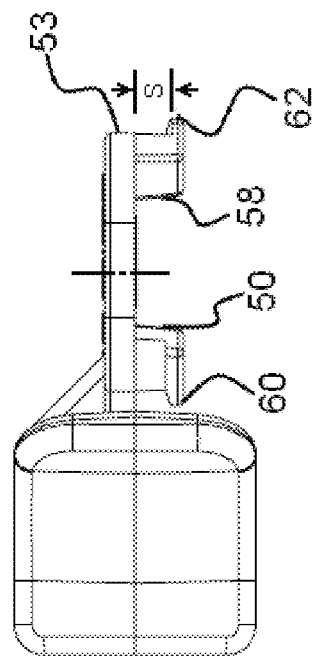

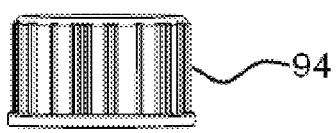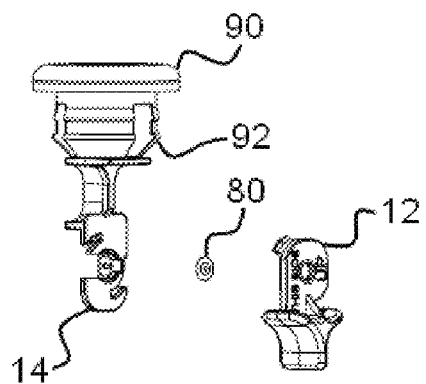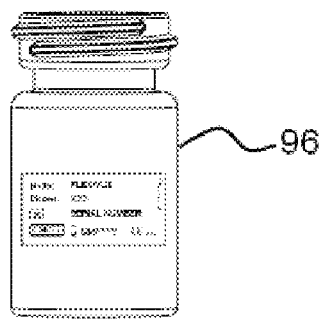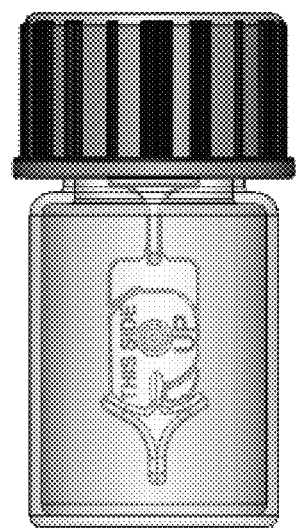
Fig. 18
Fig. 19

LENS HOLDER APPARATUS AND SYSTEM AND METHOD

BACKGROUND

1. Field of the Invention

The invention relates to holding and transport devices for holding lenses during transport and storage such as from the point of manufacture to the point of usage and to facilitate inspection and access.

2. General background

In the field of eye surgery, there are two types of eye lens implants, intracorneal and intraocular implants. In each of these a small lens is implanted into the eye in the cornea or in or adjacent the iris. The lenses are very small such as in the case of intracorneal lenses in the range from 1 mm to 4 mm in diameter and in the case of intraocular lenses in the range from 4 mm to 8 mm in diameter. From the point of manufacture to implantation the lens has to be carefully maintained in some kind of container. During the operations from manufacture, shipment and storage to implantation, handling of the lens can be detrimental and risky to the lens itself and is inconvenient for handling such small items. There is a need to reduce any transfer of the lens from one environment to another and to allow access to the lens for testing and for use with the minimum of actual handling of the lens.

BRIEF DESCRIPTION OF THE DRAWINGS

For a further understanding of the objects and advantages of the present invention, reference should be had to the following detailed description, taken in conjunction with the accompanying drawings, in which like parts are given like reference numbers and wherein:

FIG. 5 is a section view through 5-5 of FIG. 3.

FIG. 6 is an enlarged view of the circled portion A of the lower case in FIG. 3.

FIG. 7 is a section view through 7-7 of FIG. 6.

FIG. 9 is a top view of the upper case.

FIG. 10 is a front view of the upper case.

FIG. 11 is a side view of the upper case.

FIG. 18 is an exploded view of the holder apparatus, a lens held in it, the retaining plug and the bottle.

FIG. 19 is a view of the holder apparatus inside a bottle.

DETAILED DESCRIPTION

The invention is in the field of transporting eye implant lenses and the ability to conveniently test and access such lenses. Embodiments include a lens holder apparatus and a system that combines a lens holder apparatus with a container. One feature is that a lens is trapped in a lens holder apparatus for minimum movement. Another feature is to be able to inspect the lens while it is in the lens holder apparatus and also while it is in the container. The invention provides several functions that are important in the transportation, storage and testing of such lenses. The functions include protecting the lens, allowing testing of the lens while it remains retained in the holding apparatus and allowing for convenient placement of the lens into the holding apparatus and for convenient removal of the lens at the time it is to be used. Embodiments of the lens holder apparatus include two parts that define a chamber into which a lens can be placed, the two parts being separable and joinable to allow a lens to be installed and later removed. Transparent portions of the two parts are aligned so as to allow optical testing and observation of the lens. The holder apparatus also has a handle which can be fitted to a part in a bottle assembly so that it will stay in a fixed position in the bottle.

The invention will be understood from the following description in conjunction with the drawings.

Figure 1:
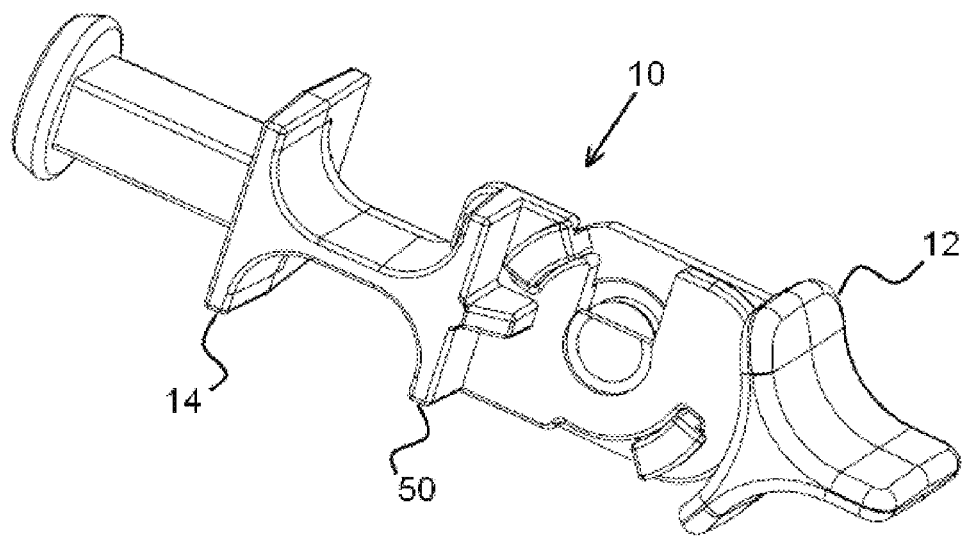
FIG. 1 is a perspective view of the assembled lens transport apparatus.
Figure 2:
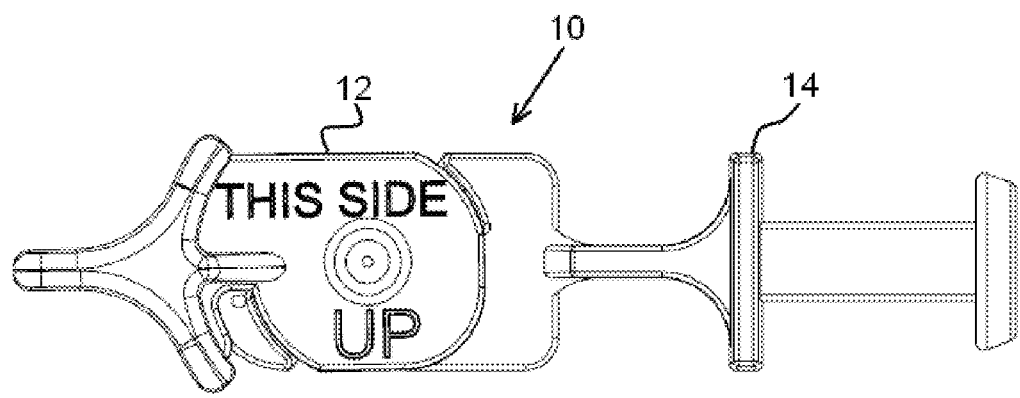
FIG. 2 is a top view of the assembled lens transport apparatus.
Figure 3:
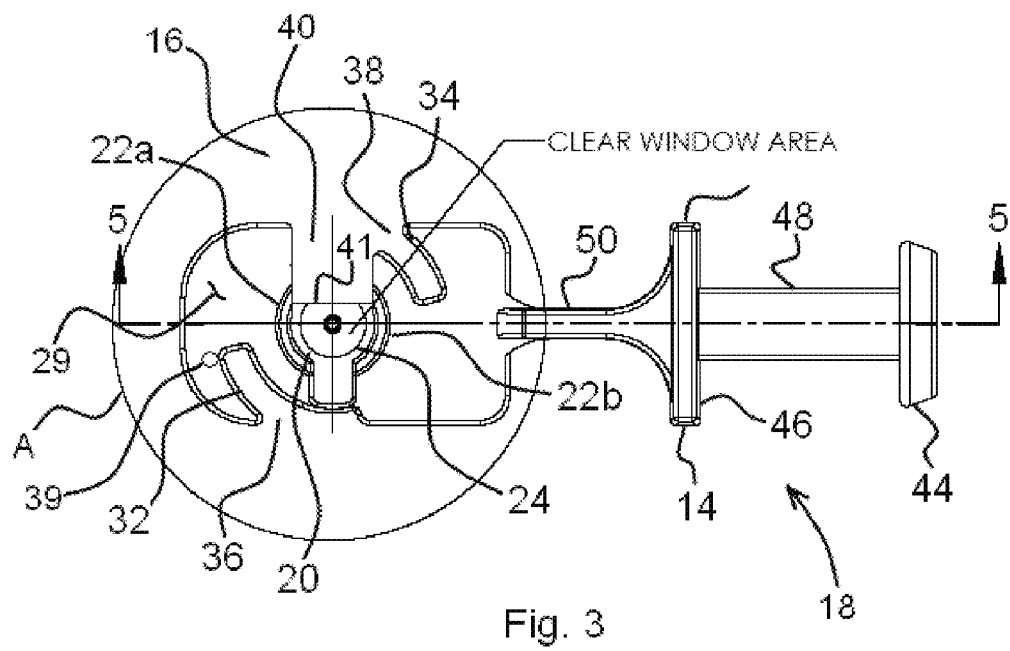
FIG. 3 is a top view of the lower case.
Figure 4:
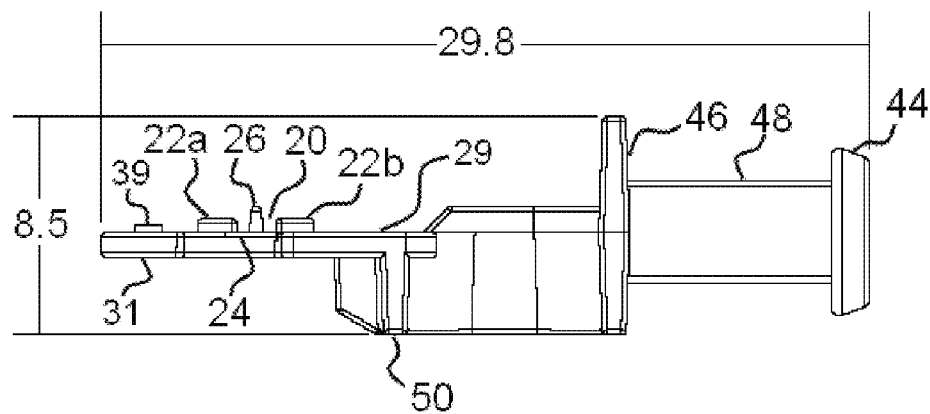
FIG. 4 is a side view of the lower case.
Figure 8:
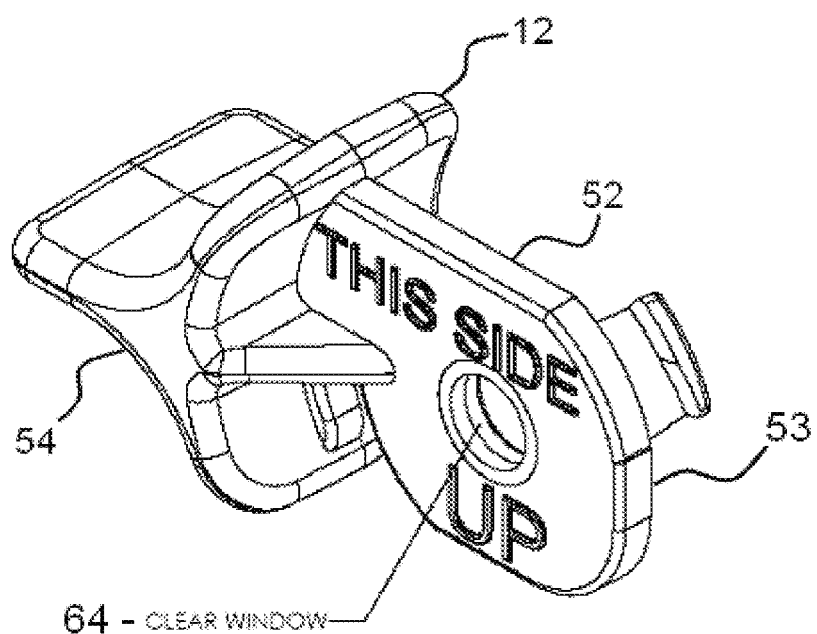
FIG. 8 is a perspective view of the upper case.

FIGS. 1 and 2 show a perspective view and a top view of the holder apparatus 10 in its assembled configuration for holding a lens. It has two parts, an upper case 12 and a lower case 14. In FIGS. 1 and 2 the holder apparatus 10 is in its fully assembled form, that is the upper case 12 and the lower case 14 are in the final position for holding a lens. In this description the term "lens" refers to all types of eye lens implants.

FIGS. 3 through 7 illustrate an embodiment of the lower case 14. The lower case 14 has a generally flat containment portion 16 (shown within the circle A in FIG. 3) and a handle portion 18. With additional reference to FIGS. 16 and 17, the containment portion 16 has a lower case space element 20 which is defined by circular partial bosses 22a and 22b. Within space portion 20 is a clear window area 24 and in its center is a post 26 which has a shoulder 28 above the window area 24. An axis 30 is defined by the center of the window area, and extending through the post 26. The window area is an integral part of the containment portion 16 and is made transparent during the molding process to make the lower case 14 in a manner known in the plastic molding art.

The containment portion 16 of the lower case 14 has an inner surface 29 and an outer surface 31 defining a thickness T. It has slots 32 and 34 that extend in a circular shape around the axis 30 and they are generally oppositely located. Each slot has an opening 36 and 38 respectively. A latch is defined by a protrusion 39, in this embodiment circular, upward from the inner surface 29. The containment portion 16 has an opening 40 extending from one side toward the axis and ending at edge 41 just into the window area 24, the opening 40 serving to facilitate removal of a lens as will be explained below. The handle portion 18 has a retainer knob 44 and a tang 46, a spacer bar 48 and support beams 50 to which the containment portion 16 is mounted.

The lower case 14 is molded from a single piece of plastic, a polysulfone; Solvay Advanced Polymers UDEL-P1700 CL2611 and UDEL P1700 NT 06 being exemplary. The clear window area 24 is made by polishing on each side. The polished surface is achieved by inserting pins with a highly polished surface in the mold.

The upper case 12 is shown in FIGS. 8-11 and FIGS. 16 and 17. It has a containment portion 52 and a handle 54. The containment portion 52 is built up from a generally flat body 53. From a lower side of the body 53 tabs 56 and 58 project. The tabs have rims 60 and 62 respectively. The rims 60 and 62 have a wedge shape commencing thinner at a front and thicker toward the rear. This wedge shape has the effect of a gradual reducing of the space S between the rim and the surface of the body 53. As will be seen, the thickness T of the containment portion 16 of the lower case 14 will be gripped in the space S so that the wedge shape accommodates the assembly to result in a secure assembly. A clear circular window area 64 defines a center at 66 in a space element 68 bounded by a circular rim 70 that defines the upper case space portion. The tabs 56 and 58 are circular around the center 66. The axis 30 runs through the center 66. The window 64 has a central aperture into which the post 26 extends when the upper and lower case are assembled. The upper case has a slot 72.

The window areas 24 and 64 (also called transparent portions) can be made integral with their respective case portions or can be made separately and installed. They are configured to allow optical testing of the lens inside the chamber.

Figure 12:
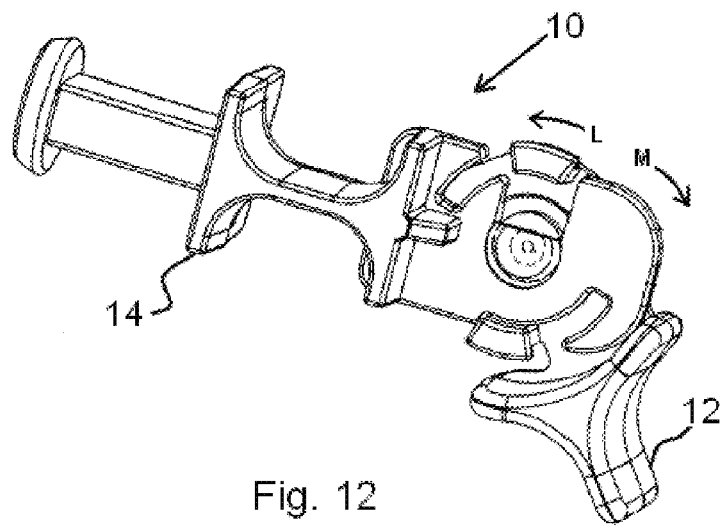
FIG. 12 is a bottom perspective view of the upper case and the lower case in the position ready for assembly.
Figure 13:
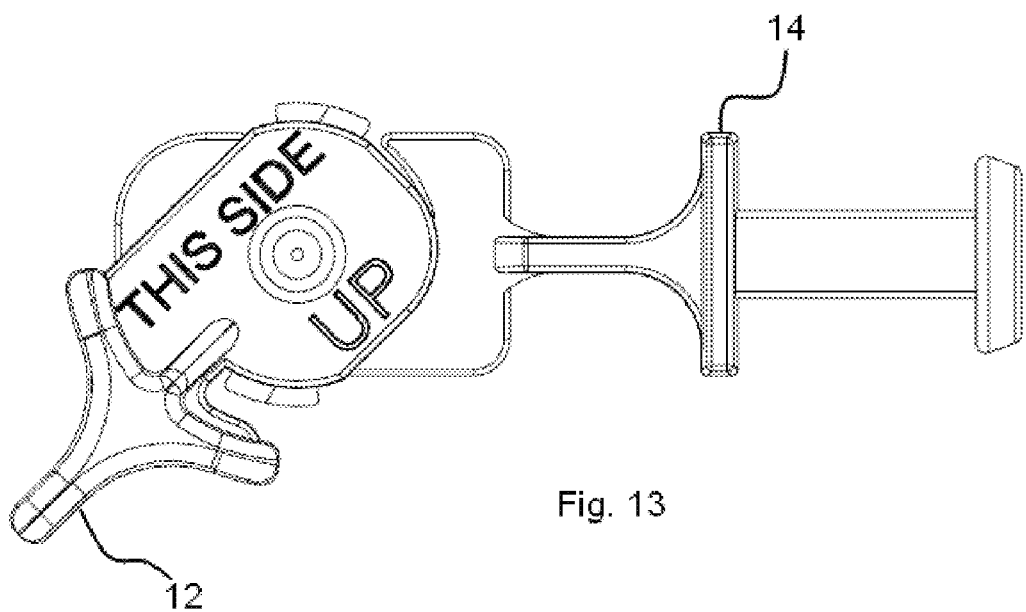
FIG. 13 is a top view of the upper case and the lower case in the position ready for assembly.
Figure 15:
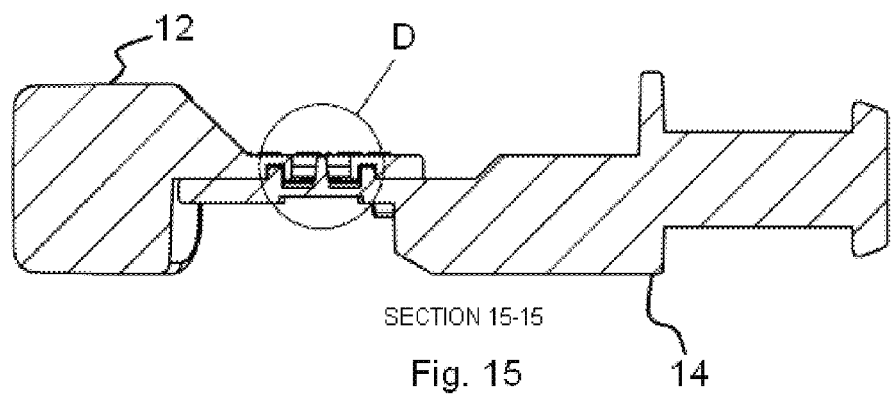
FIG. 15 is a sectional view through 15-15 of FIG. 15.

To employ the lens holder apparatus, the upper case and the lower case are connected after a lens 80 has been fitted on the post 26. The procedure for connecting them is shown in FIGS. 12 and 13. FIG. 12 is looking up from under the lower case 14. The upper case 12 is in position with the tabs 56 and 58 of the upper case adjacent the openings 36 and 38 of the slots 32 and 34 of the lower case. FIG. 13 is looking down from over the apparatus with the upper and lower cases in the same ready positions as in FIG. 12.

Figure 14:
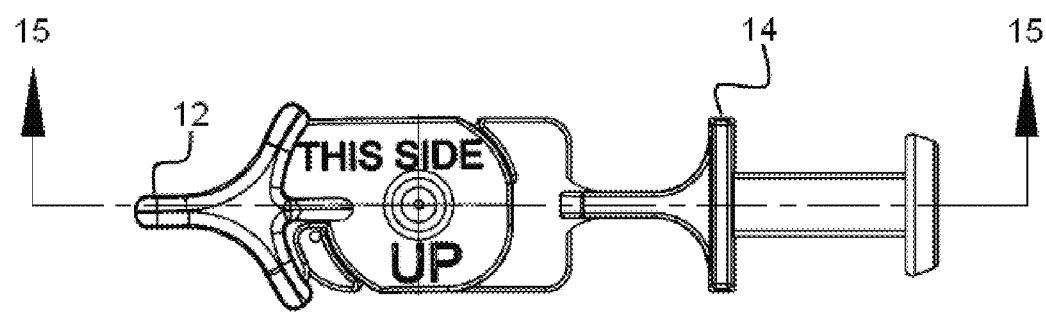
FIG. 14 is a top view of the apparatus with the upper case and the lower case in the assembled position.

To make the assembly the upper and lower cases 12 are rotated relative to each other as exemplified by arrows L and M in FIG. 12 into the final assembled position as shown in FIG. 14. Note the designation "THIS SIDE UP" on the top of upper case 12, which is an instruction to hold the parts so that the lens does not fall out before they are connected, and later for inspection and removal. In the step of rotating the upper and lower cases the tabs 56 and 58 enter the slots 32 and 34 while the rims 60 and 62 grip the containment portion 16. Also, at the end of the rotation step the latch 39 pops (a "click" can be heard) into the slot 72 to provide a positive assembled condition.

Figure 16:
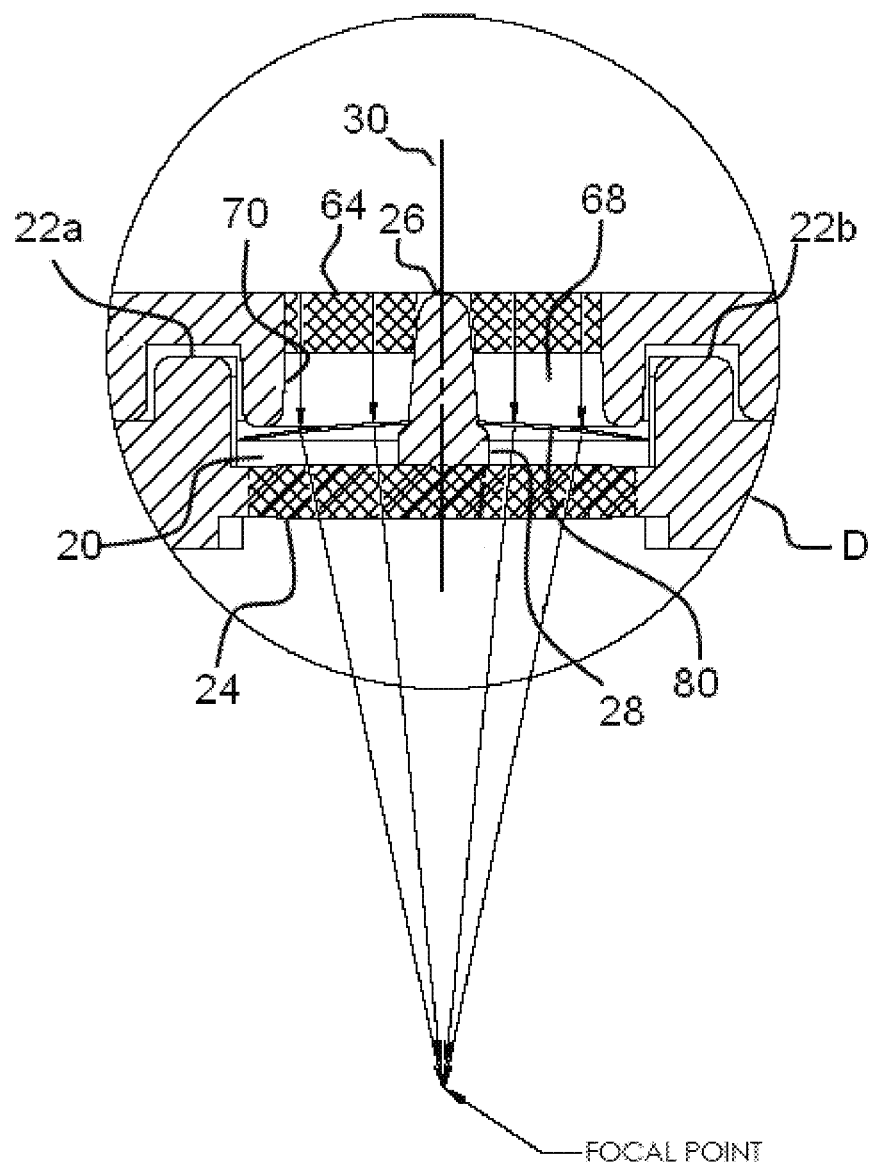
FIG. 16 is an enlarged detail sectional view of portion B of FIG. 15 showing the storage chamber with a lens.

FIG. 16 shows an enlarged sectional view D of the upper case and the lower case when assembled with a lens 80 in the storage space which is defined by the space element 20 of the lower case and the space element 68 of the upper case. A lens 80 is in place on the post 26 seated on the shoulder 28.

Figure 17:
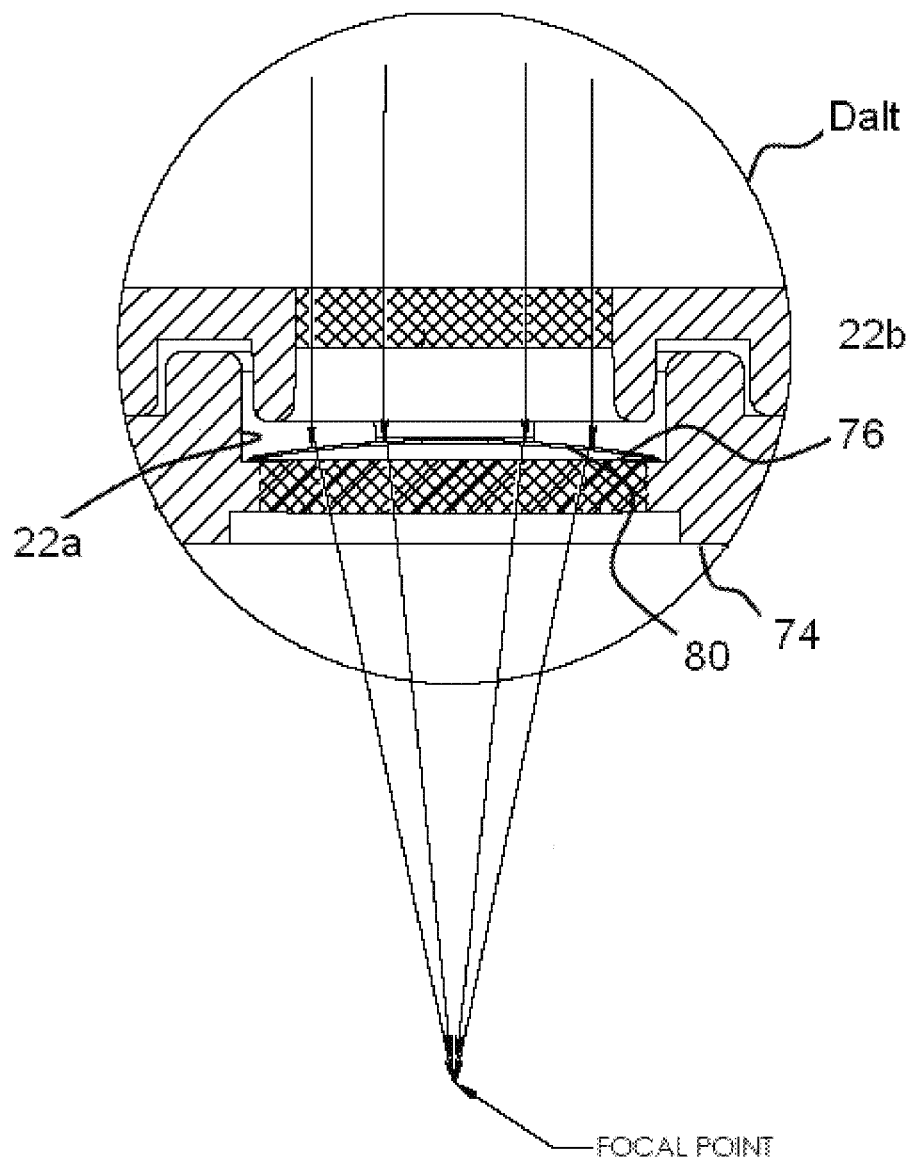
FIG. 17 is an enlarged detail sectional view of an alternative storage chamber with a lens.

An alternative embodiment is shown in FIG. 17. In this embodiment, the structure of the lower case 74 does not have a post to support the lens, instead the lens rests on the floor 76 of the lower case 74, inside the bosses 22a and 22b. Also, in this embodiment the window 64 of the upper case 12 does not have a hole. The difference in this embodiment is that the lens is not positively held, although it is sufficiently secure, as compared to the structure of FIG. 16 in which the lens is secured on the post.

When access to the lens 80 is desired, as for implanting it, a gripping device such as surgical forceps or lens insertion devices can be moved into the recess 40, with one arm above and one arm below the lens, to grip it between the arms. Thus the recess allows the arms of a gripping device access to the lens 80.

With the construction of the lens transport apparatus as described above, it can be carried in a custom made or a commercially available container. FIG. 18 shows the lens holder apparatus 10 held in a flexible plastic plug 90 by the handle portion 44 being pushed into the grip 92 of the plug 90. Then the plug 90 is installed in a bottle 96 and the cap 94 screwed on. It would also be possible to provide a container 96 as in FIG. 19 having flat sides which would allow inspection through the flat sides without the need to remove the lens holder apparatus from the container. In use the bottle would typically be filled with saline solution.

The inspection of the lens can be done using a common lensometer. The holder may be inserted in a glass cuvette filled with liquid. Such inspection methods are common for contact lenses measurement of diopter power and resolution.

Lens inspection with the invention is, for example, for optical (diopter) power, size of the lens, and cosmetics such as surface quality. In FIGS. 16 and 17 light rays are illustrated to show how measurements can be made.

After the lens transport apparatus has arrived at the point where the lens is to be implanted, the lens is removed with a device specially designed to grip it. In some cases that device will be used just to take lens out, but in most cases that device will also be the insertion device for inserting the lens into the eye. It is at this point that the recess 40 comes into use because the recess 40 allows a gripping device access to both the top and bottom of the lens to grip it and remove it.

While the invention is described in terms of a specific embodiment, other embodiments could readily be adapted by one skilled in the art. Accordingly, the scope of the invention is limited only by the following claims.

The foregoing Detailed Description of exemplary embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations within the scope of the invention will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "step(s) for . . . ."

The invention claimed is:

1. An eye implant lens holder apparatus and an eye implant lens operative to trap the lens in the lens holder to allow transport, storage and access for use with a minimum movement of the lens or contact with instruments comprising:
   an eye implant lens;
   a lens holder apparatus comprising;
      a case having a storage chamber, the case comprising an upper case portion and a lower case portion being separate parts and each having a defined axis of rotation connectable together and comprising an upper case space element and a lower case space element respectively wherein when connected the upper case space element and the lower case space element are adjacently located to define the storage chamber with their respective axes of rotation defining a coextensive axis of rotation;

a containing structure in the storage chamber to keep an eye implant lens in a substantially fixed position when installed in the storage chamber wherein the containing structure comprises a post extending upwardly centered on the axis of rotation from the lower case into the storage chamber whereby the eye implant lens having a centrally located opening can be installed on the post through the opening;

the upper case having a circular opening centered on the axis of rotation of the upper case portion;

whereby the post and the circular opening are aligned on the coextensive axis of rotation and the post will extend to terminate in the circular opening upon the upper and lower case being connected;

on one of the upper case or the lower case a pair of slots circumferentially shaped with respect to the axis of rotation, and being substantially diametrically opposite and each having an a closed end and an open end, the ends of each slot being in the same circumferential orientation;

on the other of the upper case or the lower case a pair of tabs each tab extending into circumferential alignment with a respective one of the slots when the axes of rotation are brought into alignment to define the coextensive axis of rotation and are engaged in the respective slot upon relative rotation of the upper and lower case about the coextensive axis of rotation thereby to connect the upper case portion and the lower case portion; and the lens being positioned on the post.

2. The holder apparatus of claim 1 wherein the containing structure comprises a ledge in the lower case space element on which the periphery of a lens can rest when installed in the storage chamber.

3. The holder apparatus of claim 1 further comprising on the one of the upper case or the lower case having the tabs, a detent latch and on the other of the upper or lower case a latch receiving opening into which the detent latch enters in frictional engagement when the rotation is done.

4. The holder apparatus of claim 3 wherein the slots are on the lower case and the tabs are on the upper case and the detent latch is on the lower case and the latch receiving opening is on the upper case.

5. The holder apparatus of claim 1 further comprising a handle on one of the upper case or the lower case.

6. The holder apparatus of claim 5 wherein the handle is on the lower case.

7. The lens holder apparatus and eye implant lens of claim 1 further comprising a containing apparatus for comprising a flexible plug having a cavity for receiving the handle and a bottle into which the plug is insertable such that the lens holder apparatus hangs from the plug into the bottle.

8. The holder and lens of claim 1 further comprising a transparent portion on at least one of the upper case and the lower case such that the lens is optically accessible through the at least one transparent portion.

* * * * *